(12) United States Patent
Lowrie

(10) Patent No.: US 6,492,145 B1
(45) Date of Patent: *Dec. 10, 2002

(54) VACCINE AGAINST MYCOBACTERIAL INFECTIONS

(75) Inventor: Douglas Bruce Lowrie, London (GB)

(73) Assignee: Medical Research Council, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 08/737,487

(22) PCT Filed: May 18, 1995

(86) PCT No.: PCT/GB95/01119

§ 371 (c)(1),
(2), (4) Date: Nov. 15, 1996

(87) PCT Pub. No.: WO95/31216

PCT Pub. Date: Nov. 23, 1995

(30) Foreign Application Priority Data

May 18, 1994 (GB) ............................................. 9409985

(51) Int. Cl.[7] ........................ A01N 43/04; C12N 15/00; C12C 1/00
(52) U.S. Cl. ...................... 435/93.2; 435/93.21; 514/44
(58) Field of Search ........................ 514/44; 435/320.1, 435/93.2, 93.21

(56) References Cited

FOREIGN PATENT DOCUMENTS

| WO | WO 89/12455 | 12/1989 |
|---|---|---|
| WO | WO 90/11092 | 10/1990 |

OTHER PUBLICATIONS

Zinkernagel et al, "Effector T–Cell Induction and T–Cell Memory versus Peripheral Deletion of T Cells", Immunological Reviews 131:199–223 (1993).

Microbial Pathogenesis, vol. 12, 1992 pp. 27–38, Silva et al "Mycobacterium Leprae 65HSP Antigen Expressed from a Retroviral Vector in a Macrophage Cell Line is Presented to T Cells in Association with MHC Class II in Addition to MHC Class I".

Infection and Immunity, vol. 58, No. 1, 1990 pp. 80–87, Thole et al "A Major Immunogenic 36,000–Molecular–Weight Antigen from Mycobacterium Leprae Contains an Immunoreactive Region of Proline–Rich Repeats".

International Journal of Leprosy and Other Mycobacterial Diseases, vol. 60, No. 4, Dec. 1992 pp. 659–660, Corcos "Genetic Vaccines Against Genetically Infective Macromolecules?".

The Journal of Immunology, vol. 112, No. 1, 1974 pp. 271–284, Youmans et al "The Effect of Metabolic Inhibitors and Hydroxylamine on the Immune Response in Mice to Mycobacterial Ribonucleaic Acid Vaccines".

Vaccine, vol. 12, No. 16, Dec. 1994 pp. 1537–1540, Lowrie et al "Towards a DNA Vaccine Against Tuberculosis".

*Primary Examiner*—Mark Navarro
*Assistant Examiner*—Iesha Fields
(74) *Attorney, Agent, or Firm*—Kilpatrick Stockton LLP

(57) ABSTRACT

A naked nucleic acid construct comprising a coding sequence which encodes a mycobacterial stress protein or proline-rich antigen or an antigenically effective fragment thereof operably linked to a promoter capable of expressing the said coding sequence in a mammalian host cell is useful as a vaccine against a mycobacterial infection such as tuberculosis and leprosy.

5 Claims, 5 Drawing Sheets

VACCINE AGAINST MYCOBACTERIAL INFECTIONS

This invention relates to vaccines against mycobacterial infections such as tuberculosis and leprosy.

Despite its central position in classical immunology surprisingly little is known of how a protective cell-mediated immune response is either acquired or expressed against tuberculosis or leprosy. It is not know why vaccination with live bacille Calmette-Guerin (BCG) is highly protective in only some human populations or why, in contrast to live BCG, injections of dead BCG or antigenic components, even in large amounts and with adjuvants, confer only slight protection in animals.

In an attempt to develop an alternative vaccine based on the *Mycobacterium leprae* 65 kDa heat shock protein (MLhsp65) antigen (Mehra et al (1986): Proc. Natl. Acad. Sci. USA; 83, 7014–7017), we have now stably transfected bone marrow cells with an expression vector encoding this antigen. When the transfected bone marrow cells were injected into mice, the mice were found to be resistant to infection by *Mycobacterium tuberculosis*, the causative agent of tuberculosis. Further, we have injected mice with naked DNA encoding MLhsp65 or the *Mycobacterium leprae* 36 kDa proline rich-antigen (Thole et al, Infection and Immunity (1990) 58, 80–87). These mice were also found to be resistant to infection by *Mycobacterium tuberculosis*.

These findings have general applicability. Accordingly, the present invention provides use of a naked nucleic acid construct comprising a coding sequence which encodes a mycobacterial stress protein or proline-rich antigen or an antigenically effective fragment thereof operably linked to a promoter capable of expressing the said coding sequence in a mammalian host cell, in the manufacture of a medicament for use as a vaccine against a mycobacterial infection.

The invention also provides:

such a naked nucleic acid construct for use as a vaccine against a mycobacterial infection;

a vaccine composition comprising such a naked nucleic acid construct and an acceptable carrier or diluent;

a method of vaccinating a mammalian host against a mycobacterial infection, which method comprises administering to the host an effective amount of such a naked nucleic acid construct;

bone marrow cells transfected with a nucleic acid construct comprising a coding sequence which encodes a mycobacterial stress protein or proline-rich antigen or an antigenically effective fragment thereof operably linked to a promoter capable of expressing the said coding sequence in bone marrow cells;

a method of vaccinating a mammalian host against a mycobacterial infection, which method comprises administering to the host an effective amount of such transfected bone marrow cells; and a naked nucleic acid construct as above wherein the coding sequence encodes a mycobacterial proline-rich antigen or an antigenically effective fragment thereof.

The naked nucleic acid construct comprises a coding sequence which encodes a mycobacterial stress protein or a mycobacterial proline rich-antigen or an antigenically effective fragment thereof operably linked to a promoter capable of directing expression of the said coding sequence in a mammalian host cell. Nucleic acid encoding at least one further mycobacterial protein or fragment thereof operably linked to a promoter may be included in the construct. Typically, the thus encoded further mycobacterial protein or fragment thereof will be an antigenic protein or an antigenic fragment thereof. The further mycobacterial protein or fragment thereof may be a further mycobacterial stress protein or proline-rich antigen or antigenic fragment thereof.

The naked nucleic acid construct is typically cell-free and virus-free. It is typically in isolated form. It may be purified. Although it is preferred that a construct is DNA, it may also be RNA or a modified nucleic acid. The nucleic acid may contain modifications in its backbone and possibly additions at either the 5' or 3', or both, ends of the molecule in the case of linear, as opposed to circular, constructs. This may assist in prolonging the life of the nucleic acid when taken up by host cells, for example, muscle cells which may enhance the potency of the construct. Known modifications to nucleic acid molecules include the provision of methylphosphonate and phosphorothioate backbones and addition of acridine or polylysine chains at the 3' and/or 5' ends of the molecule.

The mycobacterial stress protein encoded by the nucleic acid constructs of the present invention is generally one whose expression increases substantially when the mycobacterium from which it is derived is placed under environmental stress. Typically, the mycobacterial stress protein is a heat shock protein, for example a protein whose expression increases substantially when the bacterium from which it is derived is subjected to a high temperature, for example 42° C. or greater.

The mycobacterial stress protein is typically derived from *Mycobacterium tuberculosis, Mycobacterium leprae, Mycobacterium bovis, Mycobacterium avium* or *Mycobacterium vaccae*. Suitable proteins include the 70, 65 and 10 kDa heat shock proteins of *Mycobacterium tuberculosis, Mycobacterium leprae, Mycobacterium bovis, Mycobacterium avium* or *Mycobacterium vaccae*. Of these, the 65 kDa heat shock proteins of *Mycobacterium tuberculosis, Mycobacterium leprae* and *Mycobacterium bovis* are preferred, the heat shock proteins of *Mycobacterium leprae* being particularly preferred.

The mycobacterial proline-rich antigen may be a proline-rich antigen of *Mycobacterium tuberculosis, Mycobacterium leprae, Mycobacterium bovis, Mycobacterium avium* or *Mycobacterium vaccae*. A suitable proline-rich antigen is the 36 kDa proline-rich antigen of *Mycobacterium leprae*.

An antigenic fragment of a mycobacterial stress protein or proline-rich antigen preferably contains a minimum of five, six, seven, eight, nine, ten, fifteen, twenty, thirty, forty or fifty amino acids. The fragment may be up to ten, twenty, thirty, forty or fifty amino acids long. Alternatively, up to twenty or up to ten amino acid residues may have been omitted from the amino- and/or carboxy-terminus of the stress protein or proline-rich antigen.

The antigenic sites of the mycobacterial stress protein or proline-rich antigen may be identified using standard procedures. These may involve fragmentation of the polypeptide itself using proteolytic enzymes or chemical agents and then determining the ability of each fragment to bind to antibodies or to provoke an immune response when inoculated into an animal or suitable in vitro model system (Strohmaier et al, *J.Gen.Virol.*, 1982, 59, 205–306).

Alternatively, the DNA encoding the mycobacterial stress protein or proline-rich antigen may be fragmented by restriction enzyme digestion or other well-known techniques and then introduced into an expression system to produce fragments. These fragments may be fused to a polypeptide usually a polypeptide of bacterial origin. The resulting fragments are assessed as described previously (Spence et al, *J.Gen.Virol.*, 1989, 70, 2843–51; Smith et al, *Gene*, 1984, 29, 263–9).

Another approach is to chemically synthesise short peptide fragments (3–20 amino acids long; conventionally 6 amino acids long) which cover the entire sequence of the full-length polypeptide with each peptide overlapping the adjacent peptide. This overlap can be from 1–10 amino acids but ideally is n-1 amino acids where n is length of the peptide; Geysen et al, *Proc. Natl. Acad. Sci*, 1984, 81, 3998–4002. Each peptide is then assessed as described previously except that the peptide is usually first coupled to some carrier molecule to facilitate the induction of an immune response.

Finally, there are predictive methods which involve analysis of the sequence for particular features, e.g. hydrophilicity, thought to be associated with immunologically important sites (Hopp and Woods, *Proc. Natl. Acad. Sci.*, 1981, 78, 3824–8; Berzofsky, Science, 1985, 229, 932–40). These predictions may then be tested using the recombinant polypeptide or peptide approaches described previously.

The nucleic acid sequence encoding the mycobacterial shock protein or proline-rich antigen or fragment thereof is typically included within a replicable expression vector. Such an expression vector comprises an origin of replication so that the vector can be replicated in a host cell such as a bacterial host cell, a promoter for the expression of the nucleic acid sequence and optionally a regulator of the promoter. The vector may contain one or more selectable marker genes, for example an ampicillin resistance gene for the identification of bacterial transformants or a neomycin resistance gene for the identification of mammalian cell transformants. optionally, the nucleic acid construct may also comprise an enhancer for the promoter. The construct may also comprise a polyadenylation signal operably linked 3' to the nucleic acid encoding the functional protein. The construct may also comprise a terminator 3' to the sequence encoding the mycobacterial stress protein or fragment thereof. The construct may also comprise one or more introns or other coding sequences 3' to the sequence encoding the mycobacterial stress protein or fragment thereof. The intron or introns may be from the host organism to which the construct is to be administered or from another eukaryotic organism.

In the nucleic acid constructs the nucleic acid sequence encoding the mycobacterial stress protein or proline-rich antigen or antigenic fragment thereof is operably linked to a promoter capable of expressing the sequence. "Operably linked" refers to a juxtaposition wherein the promoter and the nucleic acid sequence encoding the mycobacterial stress protein or proline-rich antigen or fragment thereof are in a relationship permitting the coding sequence to be expressed under the control of the promoter. Thus, there may be elements such as 5' noncoding sequence between the promoter and coding sequence.

These elements may be native either to the organism from which the promoter sequence is derived or to the organism from which the mycobacterial stress protein or proline-rich antigen or fragment thereof is derived. Alternatively, the said element or elements may be native to neither the organism from which the promoter sequence is derived nor the organism from which the mycobacterial stress protein or proline-rich antigen or fragment thereof is derived. Such sequences can be included in the construct if they enhance or do not impair the correct control of the coding sequence by the promoter.

The expression vector may be of any type. For example, the vector may be in linear or circular form. It is preferred that the construct is incorporated into a plasmid vector, since it has been found that covalent closed circle (CCC) plasmid DNA can be taken up directly by muscle cells but that the DNA does not integrate into the genomic DNA of the cells (Ascadi et al, (1991): The New Biologist; 3, 71–81). Those of skill in the art will be able to prepare suitable vectors comprising nucleic acid sequences encoding mycobacterial stress proteins or proline-rich antigens or fragments thereof starting with widely available vectors which will be modified by genetic engineering techniques such as those described by Sambrook et al, (Molecular Cloning: A Laboratory Manual, 1989). Two suitable starting vectors are the plasmids pCDM8 (Invitrogen; Seed and Aruffo, *Proc. Natl. Acad. Sci. USA* (1987) 84, 3365–3369) and pHMG (Gautier et al, *Nucl. Acids Res.* (1989) 17, 8389).

Any promoter capable of directing expression of the sequence encoding the mycobacterial stress protein or proline-rich antigen or fragment thereof may be operably linked to that sequence. Particularly suitable promoters are those that direct expression in a mammalian cell. For example, promoters from viral genes that are expressed in mammalian cells such as the cytomegalovirus (CMV) immediate early gene promoter are suitable. Also suitable are promoters from mammalian genes that are expressed in many or all mammalian cell types such as the promoters of housekeeping genes. For example, the p-hydroxymethyl-CoA-reductase (HMG) promoter (Gautier et al (1989)) is particularly suitable. Also suitable are promoters and other regulatory elements of genes selectively expressed in antigen-presenting mammalian cells such as macrophages and dendritic cells.

The nucleic acid constructs are useful for gene therapy. In particular, they are useful for naked DNA vaccination of mammalian hosts against mycobacterial infections such as those caused by *Mycobacterium tuberculosis, Mycobacterium leprae* and *Mycobacterium bovis*. Accordingly, constructs comprising nucleic acid from any mycobacterial species may be prepared. Owing to the degree of conservation of some mycobacterial stress proteins, it is not always necessary to use a nucleic acid sequence from a particular species to vaccinate against infection by that species. For example, live BCG (Vacille Calmette-Guerin) cells of *Mycobacterium bovis* have long been used to vaccinate humans against *Mycobacterium tuberculosis.*

In the present invention, therefore, a nucleic acid construct encoding a stress protein or proline-rich antigen of *Mycobacterium tuberculosis, Mycobacterium leprae* or *Mycobacterium bovis* may be used to vaccinate against infection by any of these three species of Mycobacterium. For example, the present inventors have shown that constructs encoding the *Mycobacterium leprae* 65 kDa hsp or *Mycobacterium leprae* 36 kDa proline-rich antigen act as effective vaccines against *Mycobacterium tuberculosis* in mice.

A range of mammalian species can be vaccinated against mycobacterial infection using the nucleic acid constructs of the present invention. However, vaccination of humans against *Mycobacterium tuberculosis* is particularly desirable. Also desirable is the vaccination of cattle or deer against *Mycobacterium bovis*. Also desirable is the vaccination of badgers against *Mycobacterium bovis* as badgers can transmit the bacteria to cattle.

The naked nucleic acid constructs of the invention may be administered to mammals including humans by any route appropriate. Suitable routes include oral and parenteral, including subcutaneous, intramuscular, intravenous and intradermal routes.

Preferred routes of administration are oral delivery and injection, typically intramuscular or intradermal injection.

Injection of the vaccine composition into the skeletal muscle or the skin of the human or animal subject is particularly preferred. Another mode of delivery of a vaccine composition according to the invention is by a biolistic or "particle gun" method.

The naked nucleic acid constructs of the invention may be administered to the subject alone or in a liposome or associated with other delivery molecules. The effective dosage depends on many factors such as whether a delivery molecule is used, the route of delivery and the size of the mammal being vaccinated. Typical doses are from 0.1–1000 µg of the nucleic acid construct per dose, for example 1–500 µg, 50–500 µg, such as 50–75 µg, and 100–500 µg per dose.

Dosage schedules will vary according to, for example, the route of administration, the species of the recipient and.the condition of the recipient. However, single doses and multiple doses spread over periods of days, weeks or months are envisaged. Single doses typically comprise 0.1–1000 µg, for example 100–500 µg, of nucleic acid and multiple doses typically comprise 0.1–1000 µg, for example 100–500 µg, of nucleic acid each, preferably in a form suitable for intramuscular or intradermal injection. Also, single or multiple nucleic acid pellets comprising a construct according to the invention, for example pellets comprising 100–500 µg of DNA can be implanted into the recipient intramuscularly or intradermally. If the construct is administered by a biolistic method, doses will generally be at the lower end of the above mentioned ranges, owing the hight efficiency of this route. Such doses may comprise, for example, 0.1–10 µg, such as 0.1–1 µg, of the construct.

While it is possible for the naked nucleic acid constructs of the invention to be administered alone it is preferable to present them as pharmaceutical formulations. The formulations of the present invention comprise at least one active ingredient, a nucleic acid construct according to the invention, together with one or more acceptable carriers thereof and optionally other therapeutic ingredients. The carrier or carriers must be "acceptable" in the sense of being compatible with the other ingredients of the formulation and not deleterious to the recipients thereof. Liposomes may be used. Suitable liposomes include, for example, those comprising the positively charged lipid (N-[1-(2,3-dioleyloxy)propyl]-N,N,N-triethylammonium (DOTMA), those comprising dioleoylphosphatidylethanolamine (DOPE), and those comprising 3β-[N-(N',N'-dimethylaminoethane)-carbamoyl] cholesterol (Dc-Chol).

Formulations suitable for parenteral administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

It should be understood that in addition to the ingredients particularly mentioned above the formulations of this invention may include other agents conventional in the art having regard to the type of formulation in question. Of the possible formulations, sterile pyrogen-free aqueous and non-aqueous solutions are preferred. Also preferred are formulations in which the nucleic acid constructs of the invention are contained in liposomes.

Effective vaccines against mycobacterial infection by *Mycobacterium tuberculosis, Mycobacterium leprae* and *Mycobacterium bovis* can also be prepared from bone marrow cells transfected with a nucleic acid construct which encodes a mycobacterial stress protein or proline-rich antigen or fragment thereof operably linked to a promoter capable of directing expression of the said coding sequence in the said bone marrow cell.

The bone marrow cells may be transfected by any suitable method. For example the nucleic acid constructs may be packaged into infectious viral particles, for example retroviral particles. This may be done using the methodology described by Silva et al (1992): Microb. Pathogen. 12, 27–38). The constructs may also be introduced by electroporation, calcium phosphate precipitation, biolistic methods or by contacting naked nucleic acid constructs with the bone marrow cells in solution.

In the said nucleic acid constructs with which the bone marrow cells are infected, the nucleic acid may be DNA or RNA, preferably DNA.

The nucleic acid constructs with which the bone marrow cells are transfected may be of any suitable type.

Typically, the constructs will be in the form of an expression vector, such as a retrovival vector or a naked DNA expression vector as defined herein. For example, the construct may be in the form of retrovival shuttle vector derived from the widely available pZipNeo vector or from a plasmid vector as defined herein, for example pCDM8 or pHMG.

The constructs with which the bone marrow cells are transfected may comprise a coding sequence encoding at least one further mycobacterial protein or fragment thereof operably linked to a promoter capable of directing expression of the coding sequence in the mammalian cell. Typically, the thus encoded further mycobacterial protein or fragment thereof will be an antigenic protein or an antigenic fragment thereof. The further mycobacterial protein or fragment thereof may be a further mycobacterial stress protein or proline-rich antigen or antigenic fragment thereof.

The constructs with which the bone marrow cells are transfected may include any suitable promoter. Particularly suitable promoters are those that direct expression in a mammalian cell. For example, promoters from viral genes that are expressed in mammalian cells such as the cytomegalovirus (CMV) immediate early gene promoter are suitable. Also suitable are promoters from mammalian genes that are expressed in many or all mammalian cell types such as the promoters of housekeeping genes. For example, the p-hydroxymethyl-CoA-reductase (HMG) promoter (Gautier et al (1989)) is particularly suitable.

Bone marrow cells transfected with the said constructs may be administered by any suitable method, such as parenteral injection, preferably intravenous injection.

Any effective amount of bone marrow cells transfected with the said nucleic acid constructs may be administered to the recipient. Typically, from about $1 \times 10^4$ to about $1 \times 10^8$ bone marrow cells are administered, for example about from $10^5$ to $10^7$, for example $1 \times 10^6$ bone marrow cells.

The transfected bone marrow cells administered to the recipient may be of any type that is compatible with the recipient's immune system. Typically, as for any transplantation of cells or tissue, the major tissue transplantation antigens of the administered bone marrow cells will match the major tissue transplantation antigens of the recipient's cells. The administered bone marrow cells may be derived from the recipient individual.

The said transfected bone marrow cells may be delivered to the recipient alone or in any suitable formulation. A preferred formulation is a solution that is isotonic with the blood of the recipient.

The following Examples illustrate the invention. In the accompanying drawings.

Figure 1:
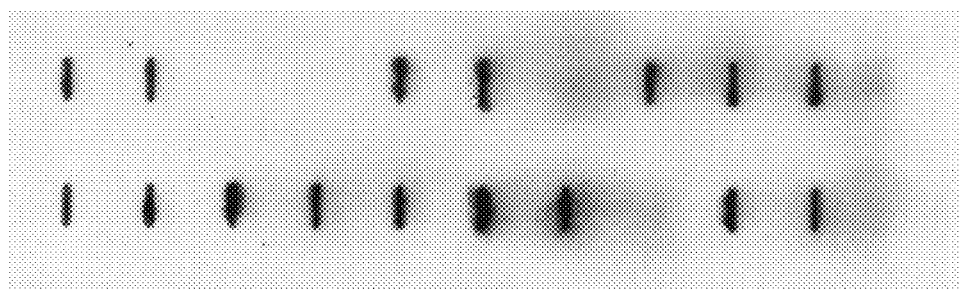
FIG. 1 shows the results of DNA Southern blot hybridisation of DNA extracted from spleen cells of Balb/c mice injected with a mixture of bone marrow cells infected with retrovirus containing MLhsp65 nucleic acid and normal bone marrow cells (1:2 ratio)
Figure 2:
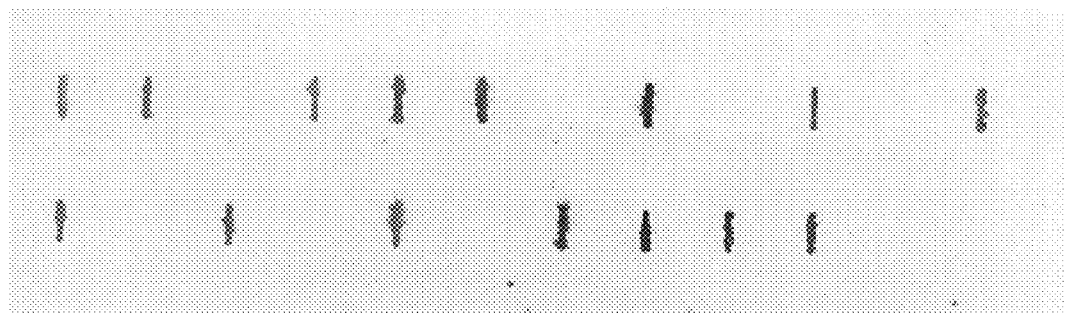
FIG. 2 shows the results of Western blot probing of protein extracted from blood samples from Balb/c mice injected with a mixture of bone marrow cells infected with retrovirus containing MLhsp65 nucleic acid and normal bone marrow cells (1:2 ratio)
Figure 3:
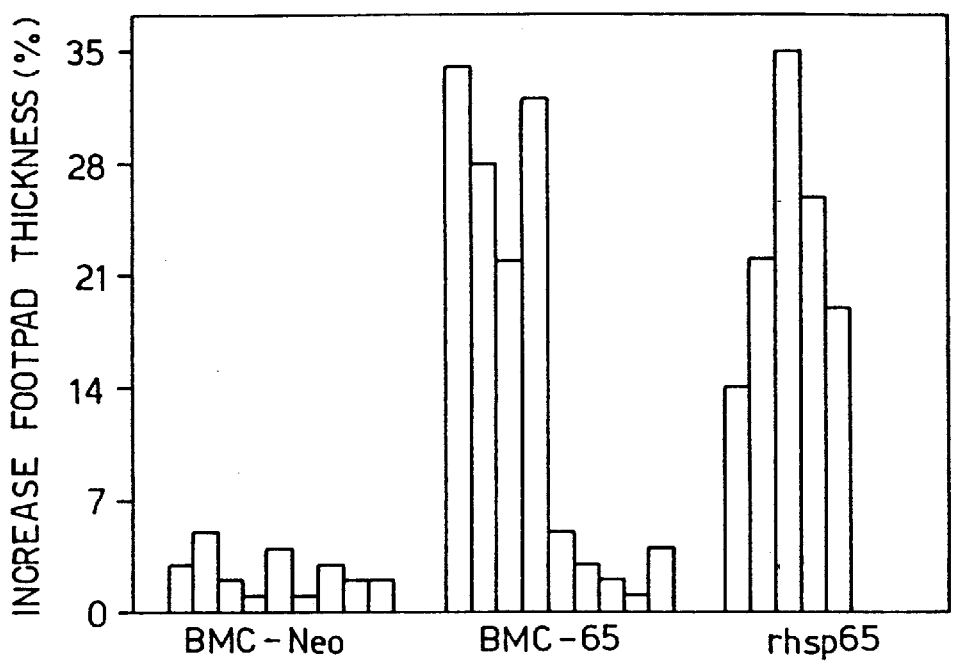
FIG. 3 shows the results of a delayed-type hypersensitivity (DTH) test on mice which had been injected with bone marrow cells infected with vector that did not contain the MLhsp65 gene (BMC-Neo), with bone marrow cells infected with retrovirus containing MLhsp65 nucleic acid (BMC-65) and with recombinant MLhsp65 (rhsp65)
Figure 4:
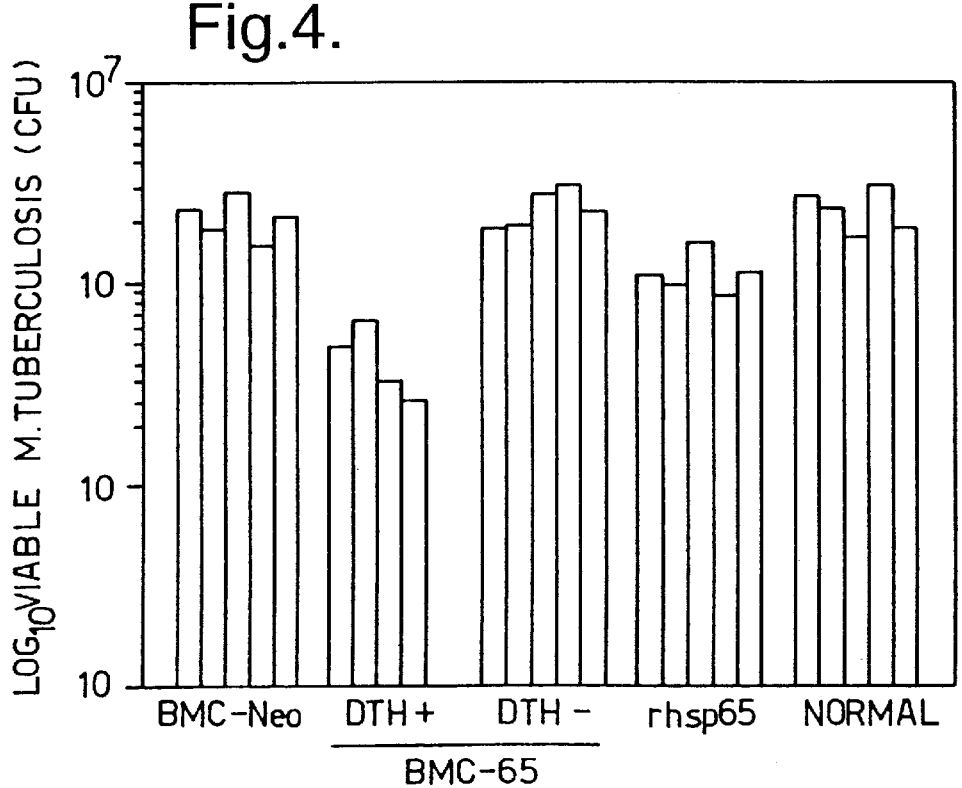
FIG. 4 shows the results of challenging with a virulent strain of M. tuberculosis the groups of mice noted in connection with FIG. 3 and an additional group immunised with rMLhsp65.
Figure 5:
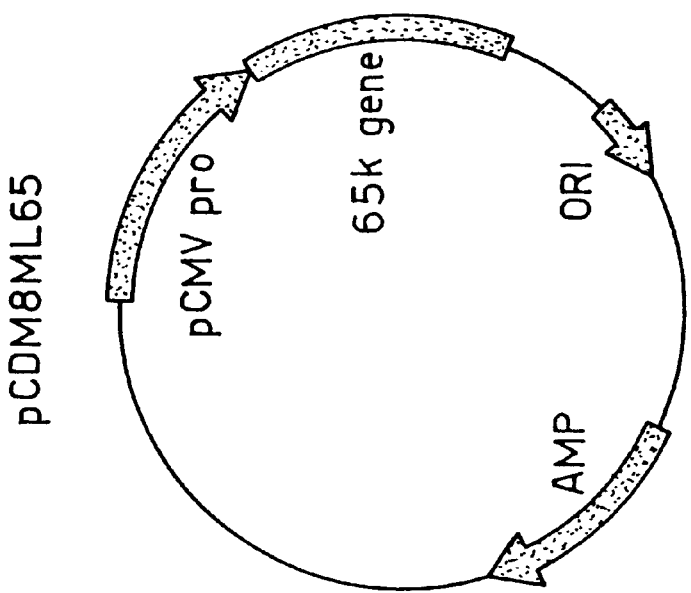
FIG. 5 depicts plasmid maps of pCDM8ML65.
Figure 5:
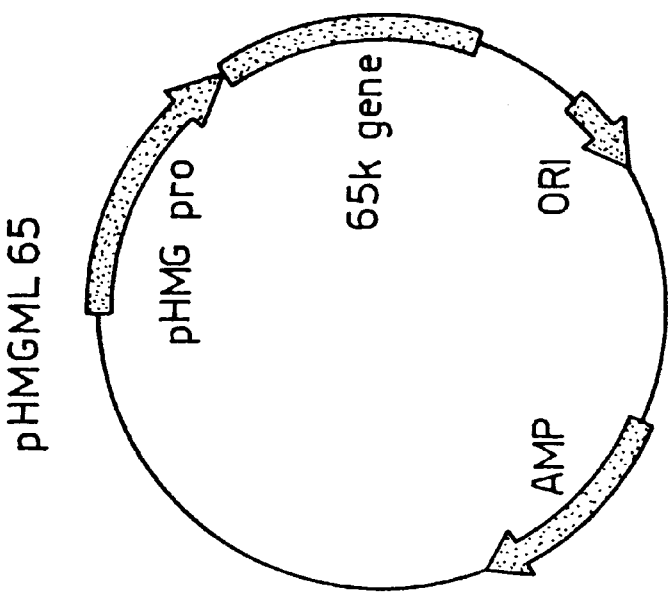
Figure 6:
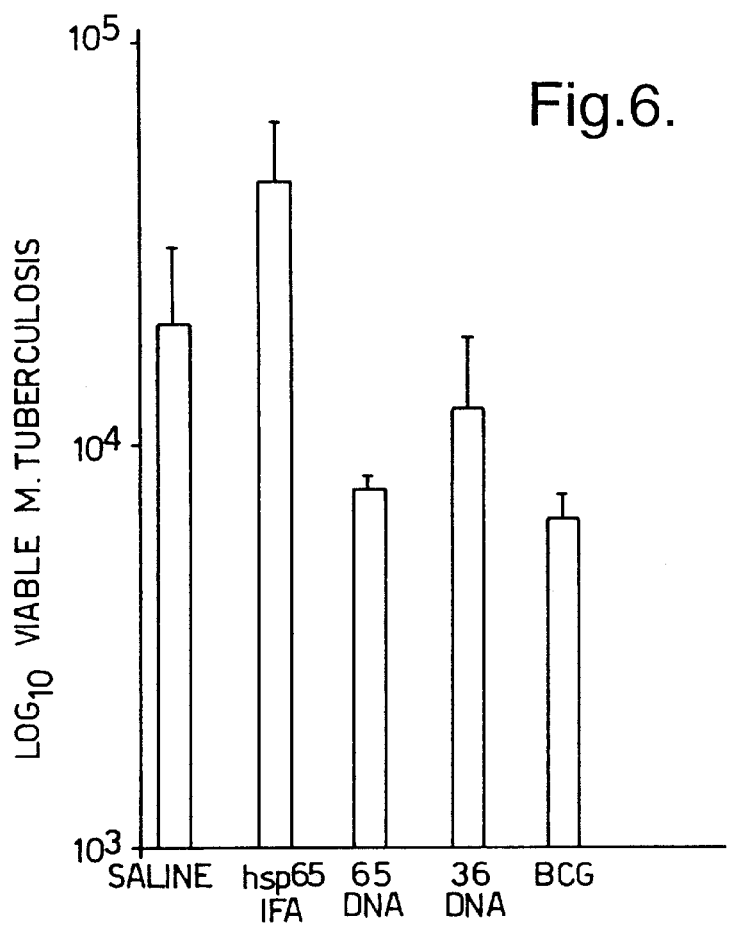

FIG. 6 shows the number of viable M. tuberculosis in livers of Balb/c mice injected with intramuscular saline (saline), rMLhsp65 and Incomplete Freund's Adjuvant (hsp65 IFA) pCDM8ML65 and pHMGML65 (65 DNA), pCDM8 and pHMG each containing the M.leprae 36 kD proline rich antigen gene (36 DNA) and M.bovis BCG;

FIG. 7 shows the number of viable M. tuberculosis in the spleen (Sp), liver (Li) and lungs (Lu) of outbred Parkes albino mice injected with pCDM8 and pHMG (control plasmid DNA), M.bovis BCG, pCDM8 and pHMG each containing the M. leprae 36 kD proline rich antigen gene (36 kD plasmid DNA) and pCDM8ML65 and pHMGML65 (65 kD plasmid DNA);

FIG. 8 shows the number of viable M. tuberculosis in the spleen (Sp), liver (Li) and lungs (Lu) of CBA/B1O mice injected with pCDM8 and pHMG (control plasmid DNA), M. bovis BCG, PCDM8 and pHMG each containing the M. leprae 36 kD proline rich antigen gene (36 kD plasmid DNA) and pCDM8ML65 and pHMGML65 (65 kD plasmid DNA);

FIG. 9 shows the number of viable M. tuberculosis in the spleen (Sp), liver (Li) and lungs (Lu) of untreated Ba1b/c mice (naive) or of Ba1b/c mice injected intradermally with pCDM8ML65 (65id), intramuscularly with pCDM8ML65 (65 im), intradermally with M. bovis BCG or intradermally with pCDM8 (control plasmid).

EXAMPLE 1

Protection Against Tuberculosis by the *Mycobacterium leprae* hsp65 (MLhsp65) Gene Expressed in Bone Marrow Cells Bone marrow cells were removed from the femurs and tibias of Balb/c mice. These cells were cultured in vitro together with pZIPhsp65 DNA which had been packaged into infectious retrovirus particles in psi-CRE cells (Silva et al (1992): Microb. Pathogen. 12, 27–38). pZIPhsp65, alternatively termed pZIPML65, contains the MLhsp65 gene and is described in Silva et al (1992). To obtain high efficiencies of infection and stable integration of viral DNA, the donor mice were first treated with 5-fluorouracil. High titres of virus ($5\times10^6$/ml) and polybrene (4 $\mu$g/ml), which promotes viral infection of the cells, were used in vitro. Infected cells were then selected by including neomycin in the culture medium (0.5 mg/ml) for 2 days.

Recipient mice were Balb/c, aged 7–8 weeks, and were irradiated (9.5 Gy) to destroy their bone marrow. They were immediately injected intravenously with $1\times10^6$ bone marrow cells. These were either a mixture of cells infected with the virus containing MLhsp65 nucleic acid, (BMC-65 cells) and normal bone marrow cells (1:2 ratio) or normal cells alone or cells that had been infected with the vector without the mycobacterial gene (BMC-Neo).

Expression of the mycobacterial gene in recipient animals was tested 15 days after transplantation by extracting DNA and protein from spleen cells and blood samples respectively. FIG. 1 shows that, by DNA Southern blot hybridization, spleen cells from 16 to 20 mice contained the MLhsp65 gene. Extracted DNA was blotted onto nitrocellulose and probed by hydridisation with a M. leprae 3.6 Kb EcoRI DNA fragment containing the MLhsp65 gene (Silva et al (1992)).

For a separate group of mice, Western blot probing with a MLhsp65-specific monoclonal antibody (CL44) revealed that 14 out of 20 had the MLhsp65 protein in their peripheral blood cells (FIG. 2). Recombinant DNA-derived protein (rMLhsp65, 20 ng) and protein extracted from blood cells of normal mice (cell lysate) were used as positive and negative controls. Bound antibody was detected with alkaline phosphatase-conjugated goat anti-mouse Ig.

30 Days after transplantation of bone marrow, other mice were tested for delayed-type hypersensitivity (DTH; footpad swelling 48 h after injection of 5 $\mu$g rMLhsp65. The results are shown in FIG. 3. All of 5 mice receiving rMLhsp65 showed DTH responses, 4 of 9 receiving BMC-65 responded and none of 9 receiving BMC-Neo did.

36 days after transplantation they were challenged by intravenous infection with $5\times10^6$ viable Mycobacterium tuberculosis H37Rv, a well-known virulent challenge strain obtained from ATCC, US. 3 weeks after that they were killed and the numbers of live bacteria in the liver was counted as colony-forming units on 7H11 agar. An additional group of control mice were immunized with rMLhsp65 in Freund's incomplete adjuvant (IFA; 25 $\mu$g) on days zero and 7, then boosted on day 14 (15 $\mu$g without adjuvant).

FIG. 4 shows that the mice that had DTH response after BMC-65 implantation were also resistant to infection with Mycobacterium tuberculosis whereas those not responding were not. A smaller amount of protection was seen in mice responding to rMLhsp65.

EXAMPLE 2

Protection Against Tuberculosis by Direct Injection of Naked Mycobacterium Leprae ap65 DNA and Mycobacterium leprae 36 kDa Proline-rich Antigen DNA into Muscle The gene encoding MLhsp65 was cloned using standard techniques into two eukaryotic expression vectors pCDM8 (Invitrogen; Seed and Aruffo, *Proc. Natl. Acad. Sci. USA* (1987) 84, 3365–3369) and pHMG (Gautier et al, Nucl. Acids Res. (1989) 17, 8389) to form pCDM8ML65 and pHMGML65 (FIG. 5). Thus, a DNA sequence comprising the MLhsp65 gene was excised from the E. coli cloning vector pUC8 using restriction endonucleases (Silva et al (1992)). This sequence was then ligated into pCDM8 and pHMG. pCDM8 and pHMG are expression vectors which are not dependent on integration into the host cell genome and carry strong promoters that are likely to function in a wide range of mouse cell types.

The constructs were purified from bulk preparations grown in E. coli by standard procedures. Normal Blb/c, CBA/B1O or outbred Parkes albino mice were injected with 50–75 μg of one construct into the left quadriceps muscle and 50–75 μg of the other construct into the right quadriceps muscle. The injections were repeated at intervals of 2–6 weeks until 4 or 5 pairs of injections had been given in a 3 to 4 month period. 2 weeks after the last injections the mice were challenged by intraperitoneal infection with $1 \times 10^6$ viable Mycobacterium tuberculosis. 6 weeks after that they were killed and the number of live bacteria in internal organs was counted as colony-forming units on 7H11 agar.

Another group of the mice was similarly injected with naked DNA composed of vectors containing, instead of MLhsp65, the Mycobacterium leprae gene for a 36kD proline-rich antigen (Thole et al, Infection and Immunity (1990) 58, 80–87).

Two naked DNA constructs containing the 36 kD proline-rich antigen were in fact prepared. A 1 kb EcoR1 fragment was excised from pTHL1007 (Thole et al (1990)). This fragment was cloned into the EcoR1 polylinker of a cloning vector, pSL301 (Invitrogen; Brosius, DNA 8, 759–777, 1989; Brosius, Methods in Enzymology 216, 469–483, 1992).

A 0.9 kb BamH1 fragment was excised from the resulting construct and cloned into the BamH1 site of pcDNA1/Neo (Invitrogen; Wang et al, Cell 67, 797–805, 1991; Spies and DeMars, Nature 351, 323–324, 1991; Seykora et al, Proc. Natl. Acad. Sci. USA 88, 2505–2509, 1991; Attaya et al, Nature 355, 647–648, 1992). The resulting construct was one of the two constructs containing the gene for the 36 kD proline-rich antigen of Mycobacterium leprae that was injected into the mice. The other construct was obtained again by excising the 0.9 kb BamH1 fragment and then cloning it into the BamH1 site of pHMG.

Finally, further groups were injected with:

saline only intramuscularly, rMLhsp65 protein in IFA as in Example 1,

Mycobacterium bovis BCG ($1 \times 10^6$ cells, intradermally on day zero), or empty vectors that did not contain inserted genes, intramuscularly.

Figure 7:
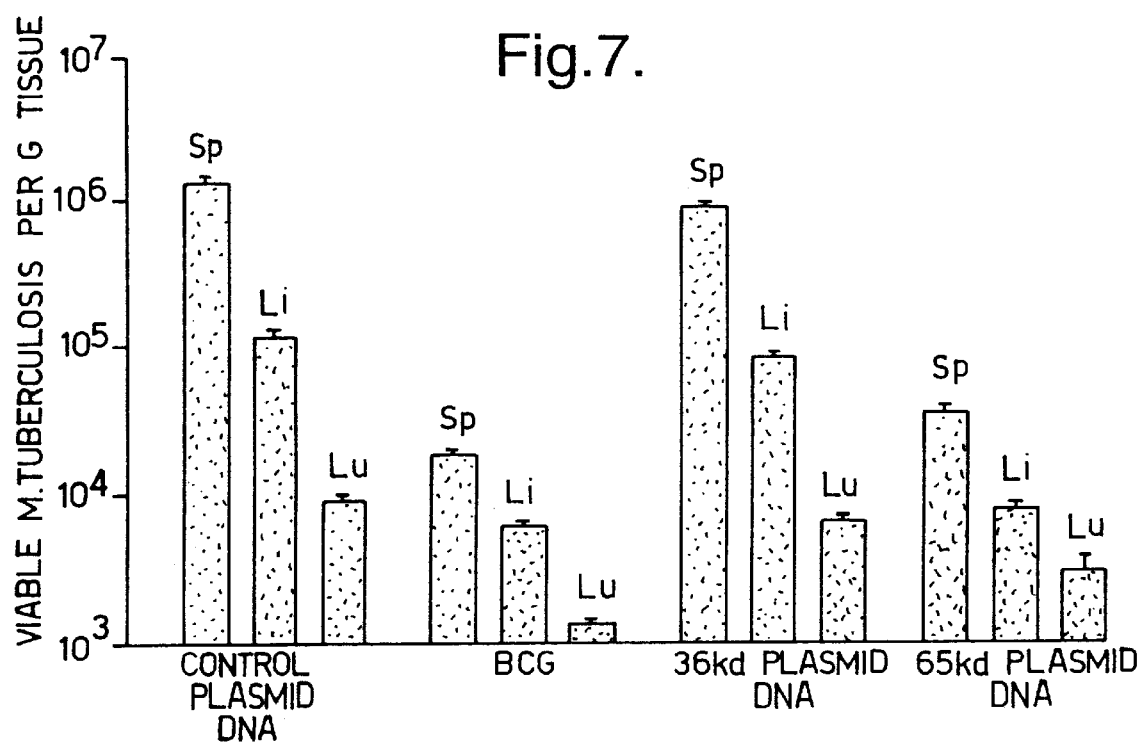
Figure 8:
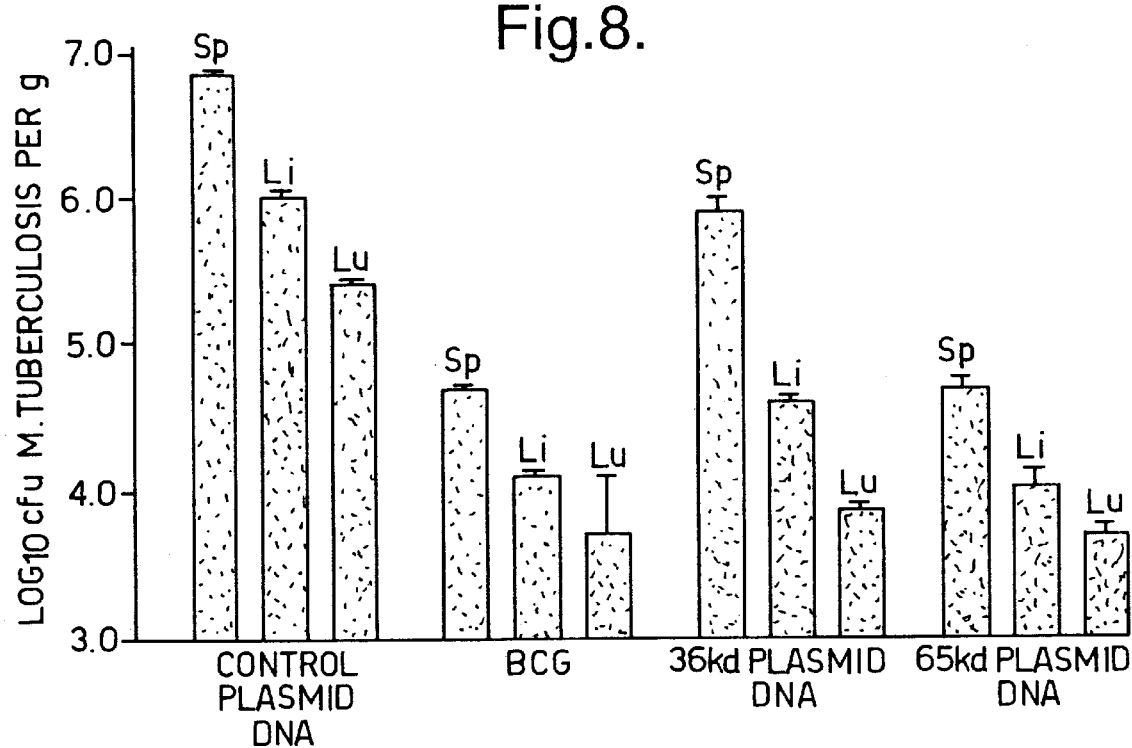

The results are shown in FIGS. 6 to 8. FIG. 6 shows that Balb/c mice were significantly protected by BCG or by MLhsp65 DNA (65DNA). The number of live bacteria in the liver of the Balb/c mice was counted in the case of the results displayed in FIG. 6. FIGS. 7 and 8 show that both CBA/B1O and the Parkes albino mice were substantially protected by BCG or by DNA containing either the MLhsp65 gene or the 36 kD proline-rich antigen gene but not by empty vectors (control plasmid DNA).

EXAMPLE 3

Figure 9:
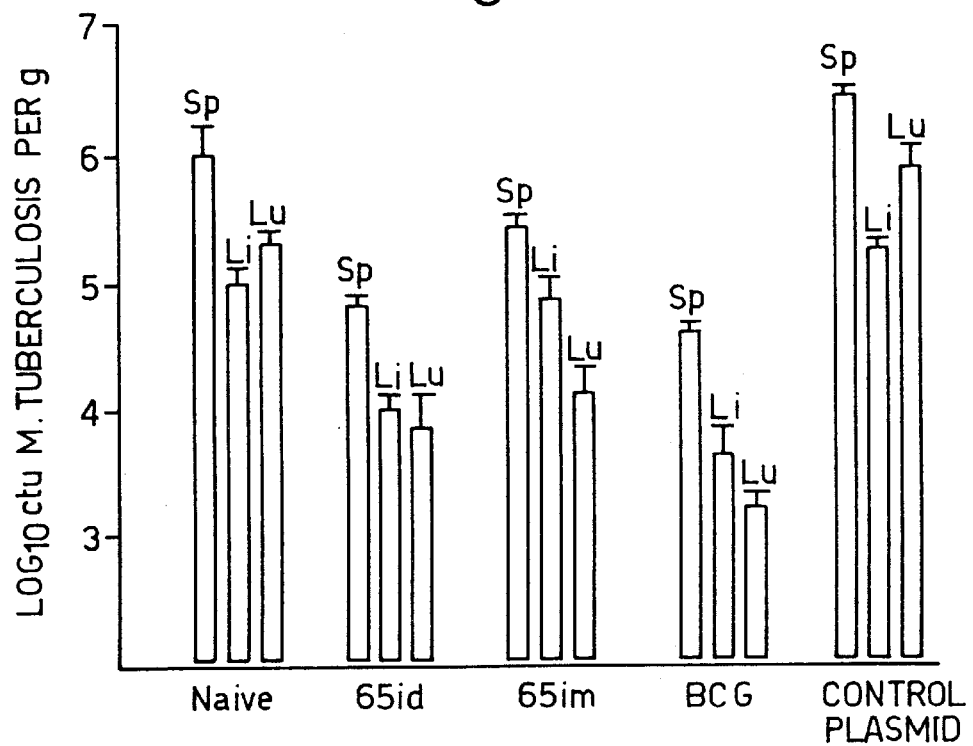

Protection Against Tuberculosis by Direct Injection of Naked Hsp65 DNA into Skin pCDM8ML65 DNA was prepared as described above. Balb/c mice were injected with 50–75 μg of the naked DNA intradermally into the base of the tail three times at 3 week intervals. Other groups of the mice were injected at the same times with 100–150 μg of the same DNA intramuscularly or with 50–75 μg of pCDM8 (vector only) intradermally. Additional control groups of the mice received live BCG intradermally as above or were untreated (naive). 8 weeks after the last DNA injections the mice were challenged by intraperitoneal infection with $1 \times 10^6$ viable Mycobacterium tuberculosis H37Rv. 4 weeks after that they were killed and the number of live bacteria in the internal organs was counted as colony-forming units on 7H11 agar. The results are shown in FIG. 9. The Figure illustrates that the intradermal route gave effective protection by pCDM8ML65 DNA.

What is claimed is:

1. A method of vaccinating a mammalian host against a mycobacterial infection, which method comprises administering to the host an effective amount of a naked nucleic acid construct consisting of a coding sequence which encodes the 65 kDa heat shock protein of Mycobacterium tuberculosis, Mycobacterium leprae or Mycobacterium bovis operably linked to a promoter capable of expressing said coding sequence in mammalian host cell, wherein the effective amount results in an immunogenic response.

2. The method of claim 2, wherein the coding sequence of the naked nucleic acid construct encodes the Mycobacterium leprae 65 kDa protein.

3. The method of claim 1, wherein the naked nucleic acid construct is a DNA construct.

4. The method of claim 1, wherein the naked nucleic acid construct is a plasmid.

5. The method of claim 1, wherein the naked nucleic acid construct is an RNA construct.

* * * * *